| United States Patent [19] | [11] 4,224,458 |
|---|---|
| Grey et al. | [45] Sep. 23, 1980 |

[54] PROCESS FOR HOMOGENEOUS HYDROGENATION OF POLYCYCLIC AROMATIC HYDROCARBONS

[75] Inventors: Roger A. Grey, Denville; Guido P. Pez, Boonton, both of N.J.

[73] Assignee: Allied Chemical Corporation, Morristown, N.J.

[21] Appl. No.: 7,877

[22] Filed: Jan. 31, 1979

[51] Int. Cl.$^2$ .................. C07C 13/28; C07C 15/24; C07C 15/28

[52] U.S. Cl. .................. 585/266; 585/268; 585/274; 585/277

[58] Field of Search .................. 585/277, 266, 268

[56] References Cited

U.S. PATENT DOCUMENTS 3,857,900   12/1974   Wilkinson .................. 585/266

OTHER PUBLICATIONS

S. Friedman et al., J. Org. Chem. 24, 1287–1290, 1959.

Paul D. Taylor et al., J. Org. Chem. 37, 3913–3915, 1972.

Michael J. Russell et al., J.C.S. Chem. Comm., 427–428, 1977.

N. Murugesan et al., Indian J. Chem. 14A, 107–111, 1976.

*Primary Examiner*—Veronica O'Keefe
*Attorney, Agent, or Firm*—Robert A. Harman

[57] ABSTRACT

An improved process is described for the homogeneous hydrogenation of polycyclic aromatic hydrocarbons utilizing anionic Group VIII metal hydride compositions as catalysts which contain phosphorus, arsenic or antimony organoligands. Use of these anionic catalysts allows the process to be conducted under mild conditions of temperature and pressure with high selectivity for the production of partially hydrogenated derivatives of polycyclic aromatic hydrocarbons such as 1,2,3,4-tetrahydronaphthalene, and eliminates the need for the presence of base or carbon monoxide atmosphere in the process.

19 Claims, No Drawings

PROCESS FOR HOMOGENEOUS HYDROGENATION OF POLYCYCLIC AROMATIC HYDROCARBONS

BACKGROUND OF THE INVENTION

1. Field of the Invention

This invention relates to an improved process for homogeneously hydrogenating polycyclic aromatic hydrocarbons thereby producing partially hydrogenated derivatives thereof, under mild conditions utilizing anionic Group VIII metal hydride compositions as catalysts.

2. Brief Description of the Background of the Invention Including Prior Art

Partially hydrogenated polycyclic aromatic hydrocarbons are known in the art as being useful organic solvents and intermediates. Particularly known are the tetrahydro derivatives, such as 1,2,3,4-tetrahydronaphthalene, also known as "tetralin."

Various processes are known in the prior art whereby fully saturated products are obtained from the homogeneous catalytic hydrogenation of aromatic and polycyclic aromatic hydrocarbons. See *J. Amer. Chem. Soc.*, Vol. 96, p. 4063 (1974); ibid., Vol. 97, p. 237 (1975); ibid., Vol. 97, p. 1266; ibid., Vol. 99, p. 7395 (1977); and *Inorganic Chemistry*, Vol. 15, p. 2379 (1976).

Relatively few processes are described for selectively producing partially hydrogenated products of polycyclic aromatic hydrocarbons under homogeneous catalytic conditions.

The reference, *J. Org. Chem.* 24, p. 1287 (1959) describes the homogeneous partial hydrogenation of polycyclic aromatics using dicobalt octacarbonyl. However, the process requires temperatures from 135°-200° C., pressures in the range of 2800-3600 psig and an atmosphere of synthesis gas, being a mixture of 1:1 molar ratio of $H_2/CO$.

The reference *J. Org. Chem.* 37, p. 3915 (1972) describes the homogeneous partial hydrogenation of anthracene producing 9,10-dihydroanthracene using cobalt hydrocarbonyl. However, the reaction requires an atmosphere of CO and $H_2$, and is not described as producing the 1,2,3,4-tetrahydro derivative of anthracene.

The reference, *J.C.S. Chem. Comm.*, p. 427 (1977) describes the homogeneous partial hydrogenation of anthracene using di-M-chlorodichlorobis(pentamethylcyclopentadienylrhodium) (I) as the catalyst. However, in the process 15 equivalents of base, (such as triethylamine) per mole of catalyst, were used and gave a mixture of tetrahydro- and octahydroanthracenes.

The reference, *Indian J. Chem.*, Vol. 14A, p. 107 (1976) describes the use of a mixture bis-(acetylacetonato) cobalt (II) and nickel (II) hydrates, treated with $LiAlH_4$ reducing agent, as capable of reducing naphthalene to tetralin and decalin. However, the process requires the in situ preparation of the catalyst, a temperature of about 150°-200° C., and reaction pressure of hydrogen of about 40-120 kg/cm² gauge (about 36-108 atmospheres).

What is desired and what the prior art does not describe are catalysts which are effective in partially hydrogenating polycyclic aromatic hydrocarbons particularly producing tetrahydro derivatives thereof, under homogeneous and mild conditions of temperature and pressure in which the presence of a basic reagent or carbon monoxide atmosphere, are not required.

SUMMARY OF THE INVENTION

We have unexpectedly found that the anionic Group VIII metal hydride compositions, described by Guido Pez and Roger Grey in U.S. application, Ser. No. 972,147 are very effective catalysts in the homogeneous hydrogenation of polycyclic aromatic hydrocarbons for producing partially hydrogenated products, and particularly the tetrahydro derivatives of polycyclic aromatic hydrocarbons. The process can be conducted under a pressure, of from 0 psig to about 150 psig and at a temperature of about 0°-150° C. The process does not require the presence of carbon monoxide atmosphere or base in the reaction medium.

In accordance with this invention there is provided a process for hydrogenating a polycyclic aromatic hydrocarbon, containing at least ten carbon atoms, compriing contacting a solution of a hydrogenation catalyst and said hydrocarbon, neat or in an inert solvent therefor, with an atmosphere containing hydrogen gas at a temperature of about 0° to 150° C. under a pressure of about 0 to 150 psig, said catalyst being a composition of the formula:

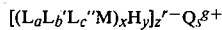

including dimers, trimers and tetramers thereof, wherein L, L' and L" are independently selected from organoligands containing phosphorus, arsenic or antimony elements, each ligand being free of carbonyl and containing at least one said element, M being a Group VIII metal, H being hydrido, Q being a cation, wherein a, b and c are integer values of 0 to 1, the sum of a, b, c being of from 1 to 3, x being a value of 1 or 2, y being an integer value of from 1 to 3x, x being defined as above, r and s independently being integer values of 1 or 2, and z and q independently being integer values from 1 to 3, wherein said composition is electrically neutral and contains a minimum of one and a maximum of three atoms of phosphorus, arsenic, antimony, or mixtures thereof, per Group VIII metal atom; thereby producing a partially hydrogenated product of said hydrocarbon.

A preferred embodiment of the process is wherein the temperature is about 80° to 100° C., the pressure is about 80-100 psig thereby resulting in the tetrahydro derivative of said hydrocarbon.

DESCRIPTION OF INVENTION AND PREFERRED EMBODIMENTS

The novelty of the invention process resides in the fact that the anionic Group VIII metal hydride compositions described in U.S. application Ser. No. 972,147 by Guido Pez and Roger Grey, hereby incorporated by reference, are very efficient catalysts for the hydrogenation of polycyclic aromatic hydrocarbons thus producing partially hydrogenated derivatives thereof. A complete and thorough description of the anionic hydride compositions, their structure, synthesis and physical properties thereof, are adequately described in the above-mentioned reference. Also, for purposes of this invention, the scope of the compositions useful as catalysts in the instant invention process is identical to the scope of the compositions disclosed in the above-described reference. By the terms "hydrogenation catalyst" and "catalyst composition" as used herein, is meant the compositions described above.

The Group VIII metals present in the compositions useful as catalysts in the invention process include iron, cobalt, nickel, ruthenium, rhodium, palladium, osmium, iridium and platinum and preferably ruthenium, rhodium, iron, and platinum, designated as M in the above-described formula.

Organoligands, independently designated L, L' and L", present in the compositions include the coordinating elements phosphorus, arsenic and antimony and preferably those of phosphorus and arsenic. The number of ligands present is 1 to 3 per Group VIII metal atom, designated by the sum of a, b and c, and the value of x, in which each ligand is carbonyl free contains at least one P, As or Sb element, and included in the total number of ligands, is a maximum of three atoms of said elements present per Group VIII metal atom in the molecule. A maximum of three atoms of P, As or Sb, or mixtures thereof, per Group VIII metal atom is a limitation because we believe that more than this number interferes in the catalytic process. For example, it has been found by us that when the anionic tris(triphenylphosphine) ruthenium complex, is employed during the homogeneous catalytic hydrogenation of ketones, additional triphenylphosphine has an adverse effect upon catalytic reactivity, wherein we believe the anionic tetrakis(triphenylphosphine) ruthenium complex is formed under the conditions.

It is also considered that carbonyl ligands generally withdraw electronic charge from the respective metal atom, to which they are attached, thus rendering any hydride ligand attached to the metal atom less hydridic in character. Since it is considered that the effectiveness of the subject compositions as homogeneous catalysts is a function of the hydridic nature of the hydride ligands, the subject compositions do not contain carbonyl ligands.

Included among ligands applicable in the compositions are those wherein L, L' and L" are independently of the formulae:

$(R'R''G_1)$, $(R'R''R'''G_1)$ and $(R'R''G_1\text{-}R\text{-}G_2\ R'''')$ wherein $G_1$, and $G_2$, are independently phosphorus, arsenic or antimony and R', R", R''' and R'''' are independently selected from $C_1\text{-}C_{18}$ linear or branched alkyl, phenyl, $C_1\text{-}C_{18}$ linear or branched alkyl-phenyl and phenyl-substituted $C_1\text{-}C_{18}$ linear or branched alkyl, and R being a $C_1\text{-}C_4$ divalent alkyl bridging group between $G_1$ and $G_2$, wherein said alkyl and phenyl groups can also be substituted with groups inert toward metal arenes (e.g. potassium napthalene), such as $C_1\text{-}C_4$ alkoxy, being linear or branched, and the like. Bidentate ligands are considered as being one ligand in the above-described formula for the subject compositions and may form two points of attachment per Group VIII metal atom, or be bridged between two Group VIII metal atoms.

Representative examples of organoligands applicable in the compositions (Ph being used hereinafter to designate phenyl) are triphenylphosphine ($Ph_3P$), diphenylmethylphosphine ($Ph_2CH_3P$), diphenylphosphide ($Ph_2P$), trimethylphosphine, triethylphosphine, triphenylarsine ($Ph_3As$), diphenylmethylarsine ($Ph_2CH_3As$), trioctadecylphosphine, tri-n-octylphosphine, triisopropylphosphine, trisecondary-butylphosphine, tricyclohexylphosphine, tri(pentamethylphenyl)phosphine, tri(p-tolyl)phosphine, tri(p-n-octadecylphenyl)phosphine, tri(p-n-octylphenyl)phosphine, tri(2-phenethyl)phosphine, tribenzylphosphine, tri(2-phenyl-isoctadecyl)phosphine, tri-(p-methoxyphenyl)phosphine, tri(2-methoxyethyl)phosphine, tri(p-tertiarybutoxyphenyl)phosphine, triphenylstibine, dimethylphosphinoethane ($Me_2PCH_2CH_2PMe_2$) and diphenylphosphinoethane ($Ph_2PCH_2CH_2PPh_2$).

Preferred ligands are those of organophosphorus and organoarsine types and particularly preferred are those of organophosphorus, particularly triphenylphosphine, diphenylmethylphosphine and diphenylphosphide.

The charge on the anion in the composition, designated as r, can be $-1$ or $-2$, and the number of anions in the composition, designated by z, can be from 1 to 3.

Cation Q in the composition has a positive charge from $+1$ to $+3$, designated by q, and the composition can have from one to three cations, designated by s. Representative examples of cations applicable in the compostion include the Group IA alkali metals, such as Li, Na, K, Rb and Cs, the Group IIA alkaline earth metals, such as Be, Mg, Ca, Ba and Sr, Group IIIA metals such as Al, and Ga, divalent and trivalent lanthanide elements such as $La^{+3}$ and $Eu^{+2}$, "metallocene" sandwich-type organo-metallic gegencations, such as $(C_5H_5)_2Ti^+$, and $(C_5H_5)_2V^+$, and divalent transition metals such as V, Cu, Mn and Fe. Preferred cations in the compositions are $K^+$, $Li^+$, $La^{+3}$ and $V^{+2}$. The total cationic and anionic charges in the composition are equivalent in absolute value such that the resulting composition is electrically neutral.

The number of hydrogen atoms, also termed "hydride" or "hydrido" ligands, attached to the Group VIII metal atoms in the compositions is from 1 to 3x, ("x" being defined above) designated by the symbol y, and can be from 1–6, and preferably two or four. It is believed that where one hydrogen atom is present per two Group VIII metal atoms, the hydrogen atom is bridged between the respective metal atoms. One of the hydride ligands present can be formed by an orthometallation process described below. The number of hydride ligands is easily established in the molecule by the well-known technique of reacting one gram mole of said composition in a pure state with at least about one gram-mole of hydrogen chloride, producing one gram-mole of hydrogen gas per gram-atom of hydride ligand present in the composition. Stoichiometrically, the reaction requires one gram-mole of hydrogen chloride, but in practice, a slight excess over this amount is used to insure complete reaction.

Representative examples of compositions applicable in the process are illustrated by the following formulas which are approximate structural formulae as regarded by us on the basis of present available evidence:

$[(Ph_3P)_3RuH]^-K^+$;  $[(Ph_3P)\ (Ph_2P)RuH]_2^-K_2^+$;
$[(Ph_3P)_2RuH]^-K^+$;
$[(Ph_2P)_2Fe_2H]^=K_2^+$;  $[(Ph_3P)_3RuH]^-Na^+$;
$[(Ph_3P)_3RuH]^-Li^+$;
$[(Ph_3P)_3RuH]_2^-Mg^{+2}$;  $[(Ph_3P)_2RuH]^-Li^+$;
$[(Ph_3P)_2RuH]^-Cs^+$;
$[(Ph_2CH_3P)_3RuH]^-K^+$;  $[(Ph_3P)_2PtH]^-K^+$;
$[(Ph_3P)_2RuH]^-K^+$;
$[(Ph_3P)_2RuH_2]^-K^+$;  $[(Ph_3P)_3RhH]^-K^+$;
$[(Ph_3P)_2RuH_3]^-K^+$.

Preferred compositions for use in the process are listed below giving their approximate structural formulas, assigned Roman numerals, used herein for convenient referral thereto, and chemical names.

| Formula | Roman Numerals | Chemical Name |
|---|---|---|
| $[(Ph_3P)_3RuH]^-K^+$ | I | potassium tris(triphenyl phosphine)ruthenium |

| Formula | Roman Numerals | Chemical Name |
|---|---|---|
| [(Ph₃P)(Ph₂P)RuH]⁻K⁺ | II | potassium triphenylphosphine diphenylphosphide ruthenium hydride |
| [(Ph₃P)₂RuH]⁻K⁺ | III | potassium bis (triphenylphosphine)ruthenium hydride |

The molecular structure of the compositions are fairly complex and have only been rigorously studied in detail in a few cases. For example, structure (I) behaves chemically as a dihydride and, on the basis of ts infrared and nuclear magnetic resonance spectra and chemical properties, can be more properly represented as being orthometallated by the formula:

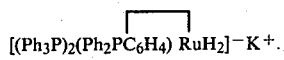

[(Ph₃P)₂(Ph₂PC₆H₄) RuH₂]⁻K⁺.

In the case of compound (II) it is felt that ortho-metallation occurs, but it is not shown in the formula since it is not known which specific phosphine (or phosphide) moiety is in fact ortho-metallated. We have shown that on the basis of chemical reactivity that the compound is a dihydride and also on the basis of proton and $^{31}P$ nuclear magnetic resonance spectra that the compound is a dimer. Thus, for purposes of this disclosure the following approximate structural formulas are considered to be equivalent:

[(Ph₃P)₂(Ph₂P)₂Ru₂H₄]⁼K₂⁺;  [(Ph₃P)(Ph₂P)RuH₂]₂⁻K₂⁺;
[(Ph₃P)(Ph₂P)RuH]₂⁻K₂⁺; and [(Ph₃P)(Ph₂P)RuH]⁻K⁺.

It is believed that other subject compositions can also exist in dimer, trimer and tetramer forms of their basic empirical formula.

It is not clearly understood, but is felt that the compositions possess the ability to undergo "ortho-metallation", a process whereby an "unfilled" coordination site on the Group VIII metal atom becomes attached by substitution onto the ortho position of a neighboring phenyl radical, for example, as present in triphenylphosphine. The bond formation between the metal atom and the ortho carbon on the phenyl ring displaces the ortho hydrogen atom, which then attaches to the metal atom thus forming a dihydride, as indicated by the horizontal bracket in the above-described formula. It is considered that "ortho-metallation" in solution is a dynamic, reversible process, in which the ortho-metallated material can react back to the non-ortho-metallated form. This ortho-metallation behavior may be present in the other catalyst compositions and can be observed by a dihydride behavior of the substance in that one gram-atom of hydride ligand in the catalyst composition will liberate one gram-mole of hydrogen gas upon reaction with at least one gram-mole of hydrogen chloride.

Other chemical characteristics of the catalyst compositions are that one gram-atom of hydrido ligand in the composition will liberate one-gram mole of methane upon reaction with at least one gram-mole of methyl iodide.

The infrared spectra of the compositions exhibit metal-hydride absorption maxima in the infrared region of about 1600 to 1900 cm⁻¹ and usually about 1750 to 1850 cm⁻¹.

The catalyst compositions can exist in the "free form" as described by the above structural formula and can also exist wherein the cation is complexed with an organic solvent in adduct form, or as a complex with a chelating agent for said cation. For example, structure I can exist as an etherate, being complexed with one mole of diethyl ether per mole of composition. The catalyst composition can also form adducts with aromatic hydrocarbons, such as naphthalene and toluene and chelates with chelating agents such as crown ethers, e.g. 18-crown-6, cryptates, being bicyclic-nitrogen bridged diamines having oxyethylene bridges, such as 2.2.2-crypt, and the like. Adducts and chelates of the compositions, in some cases, display better crystalline properties than the free-form composition, and are more convenient for handling and operability.

In addition, the chelated cation may significantly influence the catalytic activity during hydrogenation due to marked differences in ion-pairing phenomena. However, for purposes of this invention the free-form composition and adducts and chelates thereof, are considered to be equivalents as compositions and within the scope of applicable compositions.

The anionic Group VIII metal hydride compositions applicable herein can be prepared by reacting a neutral Group VIII metal complex, metal halide, hydridohalide or hydride, with a metal cationic radical anion complex, hereinafter referred to as "metal arene," such as potassium naphthalene, in a suitable solvent, such as tetrahydrofuran or diethylether, at a temperature of about −111° C. to +80° C., under vacuum or an inert atmosphere. The product is easily isolated and purified from the reaction mixture. A description of an apparatus found useful in preparing the compositions is described in J. Amer. Chem. Soc., 98, 8072 (1976), being hereby incorporated by reference.

Polycyclic aromatic hydrocarbons, and by the term is meant that at least two fused aromatic rings are present in the hydrocarbon, applicable in this improved invention process contain at least 10 carbon atoms, and preferably 10–18 carbon atoms, and can also contain substituents which are inert under the reaction conditions such as C₁–C₄ linear or branched alkyl, C₁–C₄ linear or branched alkoxy and the like. Representative examples of polycyclic aromatic hydrocarbons include acenaphthene, acenaphthylene, anthracene, 1,2-benzofluorene, 2,3-benzofluorene, benzo[ghi] perylene, benzo[a]pyrene, benzo[e]pyrene, chrysene, coronene, decacyclene, 1,2,3,4-dibenzanthracene, 1,2,5,6-dibenzanthracene, 9,10-dimethylanthracene, 1,3-dimethylnaphthalene, 1,4-dimethylnaphthalene, 1,5-dimethylnaphthalene, 2,3-dimethylnaphthalene, 2,6-dimethylnaphthalene, 9,10-diphenylanthracene, 2-ethylnaphthalene, fluoranthene, 2-methylanthracene, 9-methylanthracene, 1-methylnaphthalene, 2-methylnaphthalene, 1-methylphenanthrene, naphthalene, dinaphthyl, pentacene, perylene, phenanthrene, 9-phenylanthracene, o-phenylenepyrene, 1-phenylnaphthalene, pyrene, 2,3,5-trimethylnaphthalene, triphenylene, and alkyl and alkoxy derivatives thereof, as defined above.

Preferred polycyclic aromatic hydrocarbons in the process are naphthalene, 1- and 2-methylnapthalene, anthracene, phenanthrene and C₁–C₄ alkyl derivatives thereof.

The partially hydrogenated products resulting from the process can be the dihydro, tetrahydro, hexahydro, octahydro and decahydro derivatives of the hydrocarbons described above. Preferred derivatives produced are the tetrahydro and octahydro derivatives thereof. In general, the hydrogenation proceeds by reducing fused benzene rings in the hydrocarbon until isolated benzene rings in the hydrocarbon remain. The hydrogenation in general terminates at this point, where isolated benzene rings, are generally stable toward further hydrogenation.

In general, under the mild conditions employed in the invention process, described herein, the tetrahydro derivative is usually produced from the process, along with minor amounts of other partially hydrogenated derivatives. However, it is regarded by us that larger amounts of higher hydrogenated derivaties, such as the octahydro and decadydro derivatives can be produced under more forcing conditions of temperatures and pressure, i.e. higher values.

A preferred embodiment of the invention process is where the temperature is about 80° to 100° C., the pressure is about 80–100 psig, the atmosphere consists essentially of hydrogen gas, thereby resulting in partially hydrogenated product of said starting polycyclic aromatic hydrocarbon. Preferred is where the catalyst in the preferred embodiment is I, or II, resulting in the tetrahydro derivative of said polycyclic aromatic hydrocarbon and particularly preferred is where I is used to catalyze the hydrogenation of napthalene to 1,2,3,4-tetrahydronaphthalene.

The amount of polycyclic aromatic hydrocarbon present in the reaction medium is not critical and is generally about 1 to 100,000 parts by weight hydrocarbon per part catalyst composition, and preferably about 10–1000 parts by weight hydrocarbon per part catalyst. However, larger or smaller amounts of polycyclic aromatic hydrocarbon substrates may equally and effectively be used.

The process can be conducted in the neat state, i.e. no solvent, providing the polycyclic aromatic hydrocarbon is liquid at the reaction temperature employed and said hydrogenation catalyst is sufficiently soluble therein to initiate and maintain the hydrogenation reaction. However, it is preferred to conduct the reaction in the presence of an inert solvent for both the hydrocarbon and catalyst composition. The solubility of the respective materials in the solvent should be sufficiently large enough to initiate and maintain the hydrogenation process.

Solvents which are applicable in the invention process must be inert toward hydrogenation under the reaction conditions and possess adequate solvating ability for the substrate hydrocarbon and catalyst, should preferably be anhydrous, and include $C_6$–$C_{12}$ non-fused benzenoid hydrocarbons, $C_5$–$C_{10}$ linear or branched saturated aliphatic or alicyclic hydrocarbons, $C_4$–$C_6$ saturated aliphatic cyclic mono- or diethers $C_2$–$C_6$ saturated aliphatic linear or mono- or diethers, $C_7$–$C_{14}$ aromatic ethers, or mixtures thereof. By the term "non-fused benzenoid hydrocarbon" is meant that if more than one benzene ring is present in the hydrocarbon, they are isolated and not fused together. Thus, the term includes biphenyl but no naphthalene.

Representative examples of specific solvents useful in the invention process are benzene, toluene, m-xylene, hexamethylbenzene, biphenyl, pentane, cyclopentane, cyclohexane, methylcyclohexane, hexane, isooctane, decane, cyclodecane, tetrahydrofuran, p-dioxane, 2,5-dimethyltetrahydrofuran, methyl tetrahydrofurfuryl ether, dimethyl ether, 1,2-dimethoxyethane, diglyme, diethylether, diisopropyl ether, anisole, diphenylether, and mixtures thereof.

Preferred solvents in the invention process are toluene, benzene, cyclohexane, hexane, tetrahydrofuran, p-dioxane, diethyl ether or 1,2-dimethoxyethane. Particularly preferred solvents are toluene and tetrahydrofuran.

The amount of solvent, when used, is not critical provided sufficient solvent is present to dissolve the hydrocarbon substrate and catalyst and to initiate and maintain the hydrogenation reaction. In general, about 1 to 100 parts by weight of solvent per part of polycyclic aromatic hydrocarbon is used, although the amount is not limited thereto, and larger or smaller amounts being also effective with the above proviso.

As described above, the composition catalysts can exist in the free form or can be present as an adduct or chelate with another organic molecule. In cases where increased solubility may be desired of the catalyst composition, as for example when using $C_5$–$C_{10}$ linear or branched saturated aliphatic or alicyclic hydrocarbons, chelating agents of the type described above may be added, such as crown ethers, including 15-crown-5, 18-crown-6, dibenzo and dicyclohexyl derivatives thereof; cryptates, such as 2.2.2.-crypt; hexacyclen, the nitrogen analog of 18-crown-6 crown ether; and tertiary amines such as N,N,N',N'-tetramethylethylenediamine and the like. A preferred chelating agent is 18-crown-6. If a chelating agent is used, normally it is used in a molar ratio of chelating agent to catalyst of about 1:1 to 2:1 and preferably in slight excess over the stated 1:1 molar ratio.

Temperature in the process is normally in the range from about 0° C. to about 150° C. and preferably in the range of about 80° to 100° C. However, higher temperatures using more severe conditions can also be employed and are considered to be equivalent to the stated preferred range.

The pressure used in the process is usually about 0 psig to 150 psig at the reaction temperature and preferably about 80 to 100 psig at the reaction temperature. However, higher pressures using more severe conditions can also be employed and are considered to be equivalent to the stated preferred ranges. The term "psig" refers to pounds per square inch gauge, wherein 0 psig corresponds to 1 atmosphere and 150 psig corresponds to about 11 atmospheres.

The process is conducted under an atmosphere containing hydrogen gas, being the active reducing agent. The atmosphere is preferably free of carbon monoxide, and can also contain an inert gas such as nitrogen, argon, mixtures thereof, and the like, as long as sufficient hydrogen gas is present to maintain the hydrogenation reaction. It is preferred to conduct the process under an atmosphere consisting essentially of hydrogen gas, and particularly preferred at a pressure of abut 80–100 psig.

Conversions in the process of partially hydrogenated products range from about 30 to 100% of theory based on the starting amount of polycyclic aromatic hydrocarbon substrate.

Selectivities in the process for production of tetrahydro derivatives are in the range of about 90 to 100%, being defined as (moles tetrahydro derivative produced/divided by moles hydrocarbon hydrogenated) × 100.

Apparatus for conducting the invention process can be any conventional pressure apparatus, glass or steel, in which the operations of charging the reactant materials, heating, cooling, stirring, introduction of hydrogen gas, isolation and purification the final products can be conducted substantially in the absence of air and moisture. Such apparatus and procedure for carrying out the invention process will be obvious to one skilled in the art from this disclosure.

The partially hydrogenated product can be isolated from the process and purified by conventional methods such as extraction, fractional distillation, or column or gas chromatographic techniques.

The following examples are illustrative of the best mode of carrying out the invention as contemplated be us and should not be construed as being limitations on the scope and spirit of the instant invention.

EXAMPLE 1

Hydrogenation of Naphthalene

A glass pressure tube was charged with 40 mg of the bright yellow tris-phosphine

$[(Ph_3P)_2(Ph_2PC_6H_4) RuH_2]^- K^+$, (produced by reacting tris(triphenylphosphine) ruthenium hydridochloride with potassium naphthalene in about 1:2 molar ratio in tetrahydrofuran at $-80°$ C. under reduced pressure), 0.5 gram (3.9 mmol) of naphthalene and 5 ml of tetrahydrofuran. The reaction solution was pressurized with 90 psig of hydrogen and allowed to react in the absence of moisture and molecular oxygen, at 95° C. for 16 hours. Gas chromatographic analysis of the reaction mixture showed a 77% conversion of naphthalene to 1,2,3,4-tetrahydronapthalene as the only product.

EXAMPLE 2

Hydrogenation of Anthracene

Following the general procedure of Example 1, a glass pressure tube was charged with 40 mg of the tris-phosphine catalyst, described in Example 1, 0.5 gram (2.8 mmol) of anthracene and 3 ml of tetrahydrofuran. The reaction solution was pressurized to 90 psi of hydrogen and allowed to react at 70° C. for 2 hours. Gas chromatographic analysis of the reaction showed 1,2,3,4-tetrahydroanthracene (94%) and 1,2,3,4,5,6,7,8-octahydroanthracene (6%) as the only reduced products (93% conversion of the anthracene).

EXAMPLE 3

Hydrogenation of 2-Methylnaphthalene

Following the general procedure of Example 1, a glass pressure tube was charged with 40 mg of the tris-phosphine catalyst, described in Example 1, 0.5 gram (3.5 mmol) of 2-methylnaphthalene and 3 ml of toluene. The reaction solution was pressurized to 90 psig of hydrogen and allowed to react at 95° C. for 16 hours. Gas chromatographic analysis of the reaction mixture showed a 27% conversion to 2-methyl-5,6,7,8-tetrahydronaphthalene as the only product.

We claim:

1. A process for hydrogenating a polycyclic aromatic hydrocarbon, containing at least ten carbon atoms, comprising contacting a solution of a hydrogenation catalyst and said hydrocarbon, neat or in an inert solvent therefor, with an atmosphere containing hydrogen gas in the presence of a homogeneous hydrogenation catalyst, at a temperature of about 0° to 150° C., under a pressure of about 0 to 150 psig, said catalyst being a composition of the formula:

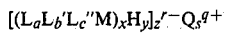

$[(L_a L_b' L_c'' M)_x H_y]_z{}^{r-} Q_s{}^{q+}$ including dimers, trimers and tetramers thereof, wherein L, L' and L'' are independently selected from organoligands containing phosphorus, arsenic or antimony elements, each ligand being free of carbonyl and containing at least one said element, M being a Group VIII metal, H being hydrido, Q being a cation, wherein a, b and c are integer values of 0 to 1, the sum of a, b, c being of from 1 to 3, x being a value of 1 or 2, y being an integer value of from 1 to 3x, x being defined as above, r and s independently being integer values of 1 or 2, and z and q independently being integer values from 1 to 3, wherein said composition is electrically neutral and contains a minimum of one and a maximum of three atoms of phosphorus, arsenic, antimony, or mixtures thereof, per Group VIII metal atom; thereby producing a partially hydrogenated product of said hydrocarbon.

2. The process of claim 1 wherein M is ruthenium, rhodium, iron or platinum.

3. The process of claim 1 wherein L, L' and L'' are independently ligands of the formula:

$(R'R''G_1)$, $(R'R''R'''G_1)$ and
$(R'R''G_1-R-G_2R'''R'''')$, wherein $G_1$ and $G_2$ are independently phosphorus, arsenic or antimony and R', R'', R''' and R'''' are independently selected from $C_1-C_{18}$ linear and branched alkyl, phenyl, $C_1-C_{18}$ linear or branched alkylphenyl and phenyl-substituted $C_1-C_{18}$ linear or branched alkyl, and R being a $C_1-C_4$ divalent alkyl bridging group.

4. The process of claim 3 wherein L, L', L'' are independently organophosphorus or organoarsine ligands.

5. The process of claim 1 wherein said cation is a metal of Group IA, IIA, or IIIA, divalent or trivalent lanthanide element, a metallocene type cation or divalent transition metal.

6. The process of claim 1 wherein said catalyst has the formula:

$[(Ph_3P)_2(Ph_2PC_6H_4)RuH]^- K^+.$

7. The process of claim 1 wherein said composition is complexed with a chelating agent therefor.

8. The process of claim 7 wherein said chelating agent is 18-crown-6.

9. The process of claim 7 wherein said chelating agent is present in a molar ratio of chelating agent to catalyst of about 2:1 to 1:1.

10. The process of claim 1 further comprising a solvent for said hydrocarbon and said catalyst.

11. The process of claim 10 wherein said solvent is a $C_6-C_8$ nonfused benzenoid hydrocarbon, or $C_2-C_{18}$ alkyl derivative thereof, $C_5-C_{10}$ linear or branched saturated aliphatic or alicyclic hydrocarbon, $C_4-C_6$ saturated aliphatic cyclic mono- or diether, $C_2-C_6$ saturated aliphatic linear or branched mono-or diether, $C_7-C_{14}$ aromatic ether, or mixtures thereof.

12. The process of claim 11 wherein said solvent is toluene, benzene, cyclohexane, hexane, tetrahydrofuran, p-dioxane, diethyl ether or 1,2-dimethoxyethane.

13. The process of claim 1 wherein said catalyst is present in an amount of about 1 to 100,000 parts of said hydrocarbon per part by weight of catalyst.

14. The process of claim 1 wherein said temperature is about 80°–100° C.

15. The process of claim 1 wherein said pressure is about 80–100 psig.

16. The process of claim 1 wherein said partially hydrogenated product is the tetrahydro derivative of said hydrocarbon.

17. The process of claim 1 wherein said polycyclic aromatic hydrocarbon contains 10–18 carbon atoms.

18. The process of claim 17 wherein said polycyclic aromatic hydrocarbon is naphthalene, anthracene, phenanthrene, and $C_1$–$C_4$ alkyl derivatives thereof.

19. The process of claim 18 wherein said hydrocarbon is naphthalene and said partially hydrogenated product thereof, is 1,2,3,4-tetrahydronaphthalene.

* * * * *